(12) United States Patent
Dalgleish et al.

(10) Patent No.: US 12,611,405 B2
(45) Date of Patent: *Apr. 28, 2026

(54) AGENT THAT INCREASES THE EXPRESSION OF THE BCL2-ASSOCIATED AGONIST OF CELL DEATH FOR THE TREATMENT OF CANCER

(71) Applicant: LDN Pharma Limited, London (GB)

(72) Inventors: Angus Dalgleish, London (GB); Wai Lui, London (GB)

(73) Assignee: LDN Pharma Limited, London (GB)

( * ) Notice: Subject to any disclaimer, the term of this patent is extended or adjusted under 35 U.S.C. 154(b) by 282 days.

This patent is subject to a terminal disclaimer.

(21) Appl. No.: 16/499,230

(22) PCT Filed: Mar. 28, 2018

(86) PCT No.: PCT/GB2018/050843
§ 371 (c)(1),
(2) Date: Sep. 27, 2019

(87) PCT Pub. No.: WO2018/178690
PCT Pub. Date: Oct. 4, 2018

(65) Prior Publication Data
US 2020/0101066 A1     Apr. 2, 2020

(30) Foreign Application Priority Data

Mar. 28, 2017   (GB) ..................................... 1704910
Nov. 14, 2017   (GB) ..................................... 1718806

(51) Int. Cl.
| *A61K 31/485* | (2006.01) |
| *A61K 45/06* | (2006.01) |
| *A61P 35/00* | (2006.01) |

(52) U.S. Cl.
CPC ............ *A61K 31/485* (2013.01); *A61K 45/06* (2013.01); *A61P 35/00* (2018.01)

(58) Field of Classification Search
CPC ........ A61K 31/485; A61K 45/06; A61P 35/00
See application file for complete search history.

(56) References Cited

U.S. PATENT DOCUMENTS

| 4,689,332 A | 8/1987 | McLaughlin et al. |
| 6,384,044 B1 | 5/2002 | Bihari |

| 8,227,483 B2 * | 7/2012 | Bao ...................... C07D 489/08 |
| | | 514/282 |
| 11,351,165 B2 * | 6/2022 | Dalgleish ............. A61K 31/675 |
| 2003/0069262 A1 | 4/2003 | Sadee et al. |
| 2003/0139352 A1 * | 7/2003 | Schoenhard ............ A61P 35/00 |
| | | 514/183 |
| 2007/0117827 A1 * | 5/2007 | Tollefson ............. A61K 31/165 |
| | | 514/618 |
| 2016/0106832 A1 * | 4/2016 | Dalgleish ................ A61P 43/00 |
| | | 424/248.1 |

FOREIGN PATENT DOCUMENTS

| EP | 1479381 A1 * | 11/2004 | ........... A61K 9/1652 |
| JP | 2008-535850 A | 9/2008 | |
| JP | 2015-107918 A | 6/2015 | |
| WO | 2006/011050 A2 | 2/2006 | |
| WO | 2006/110557 | 10/2006 | |
| WO | 2016/061531 A1 | 4/2016 | |

OTHER PUBLICATIONS

Corrie, Medicine 36:1, pp. 24-28 (2007). (Year: 2007).*
Galvez, Joelle, International Preliminary Report on Patentability, European Patent Office, PCT/GB2018/050843, May 2, 2019.
Zhang, Chaolei, First Office Action, China National Intellectual Property Administration, CN201880035530.6, Jun. 30, 2021.
Liu et al., "Naltrexone at low doses upregulates a unique gene expression not seen with normal doses: Implications for its use in cancer therapy," Int'l Journal of Oncol., 49:793-802, 2016.
Singleton, Patrick A., "The Mu Opioid Reactor: A New Target for Cancer Therapy?", Cancer, Aug. 15, 2015, pp. 2681-2688.
Umeda, Takashi, Office Action, Japanese Patent Office, Application No. 2020-503374, Aug. 23, 2022.
Harada, Takaoki, Office Action, Japan Patent Office, Application No. 2020-503374, Sep. 3, 2024.
Ueda et al., "Reconstitution of the GTP binding proteins with the opioid receptors", Biophysics, vol. 29, No. 2, pp. 346-350, 1989.

* cited by examiner

*Primary Examiner* — Amy L Clark
*Assistant Examiner* — Janet L Coppins
(74) *Attorney, Agent, or Firm* — Gavrilovich, Dodd & Lindsey LLP

(57) ABSTRACT

The present invention provides an agent that increases the expression of BAD, for use in the treatment of cancer in conjunction with a chemotherapeutic agent wherein the agent is selected from the list consisting of 6-β-naltrexol, naloxone, methyl naltrexone, or pharmaceutically acceptable salts thereof.

18 Claims, 6 Drawing Sheets

AGENT THAT INCREASES THE EXPRESSION OF THE BCL2-ASSOCIATED AGONIST OF CELL DEATH FOR THE TREATMENT OF CANCER

CROSS REFERENCE TO RELATED APPLICATIONS

This application is a U.S. National Stage Application filed under 35 U.S.C. § 371 and claims priority from International Application No. PCT/GB2018/050843, filed Mar. 28, 2018, which application claims the benefit of Great Britain Application Nos. 1704910.7, filed Mar. 28, 2017 and 1718806.1, filed Nov. 14, 2017, the disclosures of which are incorporated herein in their entirety by reference.

FIELD OF THE INVENTION

The invention relates to agents that increase the expression of tumour biomarkers for use in the treatment of cancer in conjunction with a chemotherapeutic agent.

BACKGROUND OF THE INVENTION

The success of many cancer therapies is predicated by co-administration alongside adjuvant-type molecules. Without any independent therapeutic utility, adjuvants are responsible for priming the immune system of a subject such that the active compound targeting the cancer can achieve maximum therapeutic effect.

As adjuvants typically modulate the immune response of a patient, they are used most commonly in conjunction with cancer vaccines or biologics such as humanized therapeutic antibodies. They act either to enhance the immune system of a patient to increase the production of antibodies in response to challenge with a cancer vaccine, or by suppressing or lowering the immunogenicity of the patient towards a foreign therapeutic antibody. Thus, adjuvants play an important role in driving immune cancer therapies towards a successful therapeutic outcome.

Often, immunotherapies will be combined with more traditional cancer therapies such as radiotherapy or chemotherapy. For certain types of cancers where there exists no efficacious immunotherapy, only traditional therapies can be administered. Traditional cancer treatments can also be administered in combination, where the therapeutic effect can be greater upon co-administration than the sum of the effects upon independent administration.

Despite the greater efficacy, the combination of traditional cancer therapies can exacerbate side-effects experienced by the patient, often resulting in early termination of the treatment regimen. Thus the beneficial synergistic effect of co-administering multiple anti-cancer agents can go unrealised due to the harsh nature of the therapy.

The development of new treatments with greater efficacy and reduced side effects would circumvent the need to co-administer certain cancer therapies, thus avoiding the harsh side-effects that often lead to premature treatment termination. Alternatively, the development of adjuvant-like molecules that boost the therapeutic efficacy of chemotherapeutic agents would achieve a similar outcome.

Thus, there is a need to develop agents that boost the therapeutic utility of chemotherapeutic agents in order to minimize the detrimental side effects of what would otherwise be aggressive cancer treatment regimens.

SUMMARY OF THE INVENTION

It has been found by the present inventors that agents that boost the expression of Bcl2-associated agonist of cell death (BAD) can enhance the cytotoxicity of chemotherapeutic agents in multiple cancer cell lines. The increase in overall cytotoxicity is independent of the cytotoxicity of the agent that increases the expression of BAD, which itself has no or minimal cytotoxic effect.

According to a first aspect of the invention, there is provided an agent that increases the expression of BAD, for use in the treatment of cancer in conjunction with a chemotherapeutic agent.

According to a second aspect of the invention, there is provided a method of selecting a subject having cancer for treatment with an agent that increases the expression of BAD, comprising the steps of: (a) obtaining a sample from the subject suspected in need thereof: (b) measuring the concentration of BAD within the sample; and (c) comparing the measured concentration of BAD to a reference value, wherein if the subject has a BAD concentration roughly equivalent to or less than the reference value, the subject is selected for administration with an agent that increases the expression of BAD.

According to a third aspect of the invention, there is provided a method of screening for an agent that increases the expression of BAD for use according to the first aspect of the invention, comprising the steps of: (a) incubating cells with a test agent; (b) measuring the concentration of BAD after incubation with the test agent; and (c) comparing the fold-change in expression of BAD between the cells and a control value, wherein if the fold-change in expression of BAD is at least 10%, the agent is identified as an agent for use according to the first aspect of the invention.

According to a fourth aspect of the invention, there is provided a method of treatment of a subject having cancer comprising administration of an anti-cancer agent, characterised in that the subject to be treated has an increase of 10% in the level of expression of BAD in tumour cells, relative to a control.

DESCRIPTION OF THE DRAWINGS

The invention is further defined by reference to the following drawings, in which.

DETAILED DESCRIPTION OF THE INVENTION

Figure 1A:
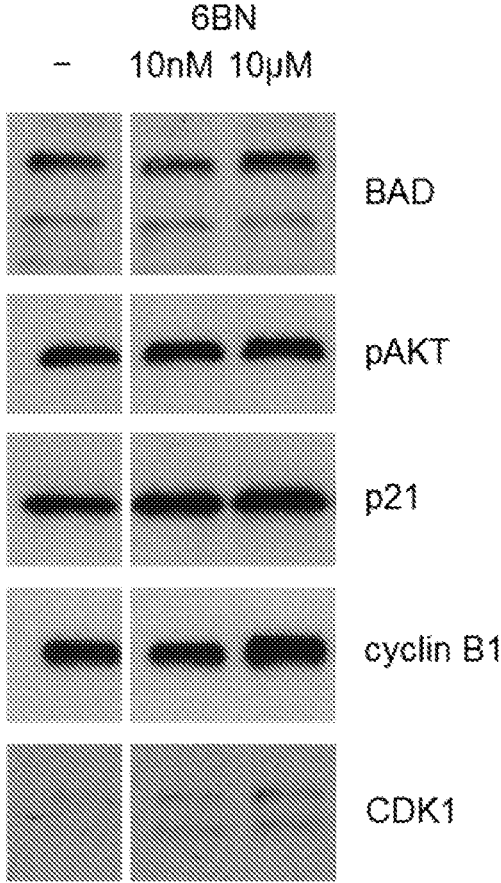
FIGS. 1a and b shows the effect of different concentrations of 6-β-naltrexol on the level of expression of BAD, p21, pAKT, cyclin B1 and CDK1 in HCT116 cells.
Figure 1B:
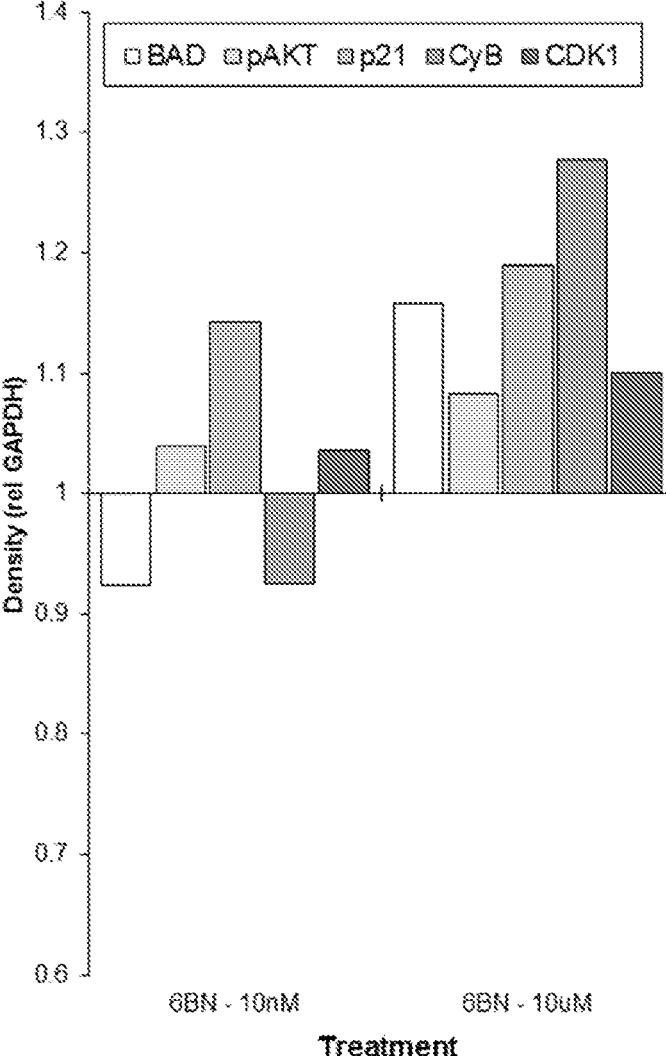

The invention is based on the finding that agents that increase expression of BAD increase the sensitivity of cancer cells to chemotherapeutic agents. This is exemplified by the use of 6-β-naltrexol. Thus, co-administration of 6-β-naltrexol together with a chemotherapeutic agent can boost the therapeutic efficacy of an anti-cancer treatment regimen. By increasing therapeutic efficacy, 6-β-naltrexol can prevent the need to implement particularly aggressive therapeutic strategies that often manifest with hazardous side-effects to the subject. Moreover, the effect of increasing efficacy could rescue particular chemotherapeutic agents that have shown limited efficacy in the treatment of particular cancers.

The inventors have found that the activity of 6-β-naltrexol is independent of any cytotoxic activity. Thus, while in isolation 6-β-naltrexol has a negligible therapeutic effect, the agent can be used to enhance cytotoxicity of chemotherapeutic agents with which it is co-administered. The ability of 6-β-naltrexol to enhance therapeutic activity is observed in at least three independent cell lines using at least two distinct classes of chemotherapeutic agents, thus suggesting that the effects of 6-β-naltrexol are applicable to boosting the therapeutic efficacy of multiple chemotherapeutic agents for use in the treatment of multiple cancers.

Without wishing to be bound by theory, 6-β-naltrexol appears to alter the phenotype of the cancer cell in such a way as to increase the sensitivity of the cell to chemotherapeutic agents. One particular marker the expression of which is altered in response to 6-β-naltrexol is BAD. Thus, the level of expression, or, as used interchangeably herein, "the level", of BAD can be used to determine that a cancer cell is sensitized to the subsequent administration of an anticancer agent. It is therefore envisaged that any agent that increases the expression BAD could be used to increase the sensitivity of a cancer cell to a chemotherapeutic agent.

The invention can be further understood with reference to the following definitions:

As used herein "6-β-naltrexol" refers to 17-(Cyclopropylmethyl)-4,5-epoxymorphinan-3,6 beta,14-triol (CAS No. 49625-89-0) and pharmaceutically acceptable salts, solvates, hydrates, stereoisomers, clathrates and prodrugs thereof. 6-β-naltrexol is a major active metabolite naltrexone. The term 6-β-naltrexol also encompasses functionally equivalent analogues thereof and metabolites that retain functional equivalence with respect to the novel uses of 6-β-naltrexol embodied within the invention.

As used herein, "increasing the expression" and synonyms thereof refer to an increase in the level of expression (i.e., the "level") of particular cellular biomarkers upon administration of 6-β-naltrexol. The increased level of expression of specific cellular biomarkers indicates the cancer cell has undergone a desired response upon administration with a first agent and is thus sensitized to the cytotoxic effect of a chemotherapeutic agent. The level of expression of biomarkers can be measured in a sample using any number of analytical methods available to the skilled person, including, but not limited to, gel electrophoresis and Western blot analysis, 2D-PAGE, column chromatography, ribosome profiling or mass spectrometry. The increased level of expression can be determined by comparing the level of expression of the biomarker from before or after administration of 6-β-naltrexol. The level of expression of the biomarker before administration of 6-β-naltrexol can be referred to as the control. In some instances, and for the measurement of particular biomarkers, it may be desirable to purify the biomarker from the cellular milieu prior to analysing the level of expression. The type of purification strategy used will be dependent on the type of biomarker being analysed. In general, techniques for the purification of biomarkers are well known to the skilled artisan and a non-exhaustive list of techniques can be found in: Protein Purification Techniques, Second Edition, Simon Roe, Oxford University Press (2001), which is hereby incorporated in its entirety.

A biomarker of particular interest in the context of the invention is BAD. BAD, also known as Bcl2-associated agonist of cell death, is a member of the BH3-only proapoptotic protein family, which initiate cell death upon activation, their activity being largely regulated by post-translational modifications which integrate a variety of cell survival or death signals (Danial 2009). BAD specifically promotes apoptosis through the binding and neutralisation of its anti-apoptotic partners BCL-2, BCL-$X_L$ and BCL-W, located in the mitochondria, where BAD translocates (from the cytosol) upon the withdrawal of growth factor survival signals. The present invention illustrates that levels of BAD are increased in response to 6-β-naltrexol administration. It is envisaged that any molecule that increases the level of expression of BAD is encompassed within this aspect of the invention. Preferably, any agent at any dosage regime that increases the level of expression of BAD by at least 5%, or at least 10%, or at least 20%, or at least 30%, or at least 40%, relative to the control, is encompassed within an embodiment of the invention. More preferably, the agent increases the level of expression of BAD by at least 10% relative to a control. More preferably, the agent increases the level of expression of BAD by from 25% to 100% relative to a control.

As used herein, the term "subject" refers to any animal (for example, a mammal), including, but not limited to, humans, non-human primates, canines, felines, rodents, and the like, which is to be the recipient of a treatment in which an agent that increases the expression of BAD is to be used according to the present invention. Typically, the terms "subject" and "patient" are used interchangeably herein in reference to a human subject.

As used herein, "chemotherapeutic agent" has its conventional meaning used in the art. The terms "chemotherapeutic agent" and "anti-cancer agent" are herein used synonymously.

According to a first aspect of the invention, there is provided an agent that increases the expression of BAD, for use in the treatment of cancer in conjunction with a chemotherapeutic agent, whereby "conjunction" means that the agent forms part of an anti-cancer treatment regimen along with a chemotherapeutic agent.

In certain embodiments, the agent is to be administered in an amount effective to increase the expression of BAD by at least 5%, or at least 10%, or at least 20%, or at least 30%, or at least 40%, relative to a control. Preferably, the agent is to be administered in an amount effective to increase the level of expression of BAD by at least 10% relative to the control. In certain embodiments, the control is the level of expression of BAD in a sample obtained from the subject prior to the administration of the agent. One of ordinary skill in the art would be able to determine such effective amounts by performing routine laboratory experiments to measure the increase in the level of expression of BAD in response to administration of increasing amounts of an agent. In certain embodiments, the biological sample obtained from the subject for use in the method is blood, plasma, serum, lymph fluid, a tissue, or cells derived from a tissue sample. Preferably, the sample is obtained from a tumour biopsy of the subject. Conventional techniques for obtaining any of the above biological samples from a subject are well known to the person skilled in the art.

Preferably, the agent that increases the expression of BAD is selected from the list consisting of 6-β-naltrexol, naloxone, methylnaltrexone, or pharmaceutically acceptable salts thereof. Preferably, the agent is 6-β-naltrexol, or a pharmaceutically acceptable analogue thereof.

In certain embodiments, where the agent is 6-β-naltrexol, 6-β-naltrexol is to be administered in an amount effective to increase the blood plasma concentration of 6-β-naltrexol to at least 0.34 ng/ml, or at least 3.4 ng/ml, or at least 34 ng/ml, or at least 340 ng/ml. In certain embodiments, 6-β-naltrexol is to be administered in an amount effective to increase the blood plasma concentration of 6-β-naltrexol to within the range of 0.3 ng/ml to 3,400 ng/ml, preferably to within the range of from 34 ng/ml to 3,400 ng/ml more preferably 340 ng/ml to 3,400 ng/ml. The amount effective to achieve such an amount can be determined using any number of conventional techniques known to the person skilled in the art. For example, the skilled person could perform mass spectrometry on a blood plasma sample obtained from the subject in order to determine the increase in the concentration of 6-β-naltrexol within the sample after administration of an amount of 6-β-naltrexol. The effective amount is the amount determined to bring about the desired increase in blood plasma concentration.

As used herein, the terms "treating" and "treatment" and "to treat" refer to both 1) therapeutic measures that cure, slow down, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In some instances, a subject is successfully "treated" for a tumour/cancer according to the present invention if the subject shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

As used herein, the term "tumour/cancer" refers to any mass of tissue that results from excessive cell growth, proliferation and/or survival, either benign (noncancerous) or malignant (cancerous), including pre-cancerous lesions. The terms "tumour/cancer" and "neoplasm" may be used interchangeably. The term "tumour cell" refers to a cells or cells derived from the tumour/cancer.

As used herein, the term "cancer cell" refers to a cell or immortalized cell line derived from tumour or cancer.

In certain embodiments, the agent that increases the expression of BAD may be administered simultaneously, separately, or sequentially alongside the chemotherapeutic agent.

As used herein, the terms "concurrent administration" or "concurrently" or "simultaneous", "sequential" or "separate" mean that administration of the agent that increases the expression of BAD and the chemotherapeutic agent occur as part of the same treatment regimen.

"Simultaneous" administration, as defined herein, includes the administration of the agent that increases the expression of BAD and the chemotherapeutic agent within about 2 hours or about 1 hour or less of each other, even more preferably at the same time.

"Separate" administration, as defined herein, includes the administration of the agent that increases the expression of BAD and the chemotherapeutic agent, more than about 12 hours, or about 8 hours, or about 6 hours or about 4 hours or about 2 hours apart.

"Sequential" administration, as defined herein, includes the administration of the agent that increases the expression of BAD and the chemotherapeutic agent each in multiple aliquots and/or doses and/or on separate occasions. The agent that increases the expression of BAD may be administered to the subject before or after administration of the chemotherapeutic agent. Alternatively, the chemotherapeutic agent is continued to be applied to the subject after treatment with the agent that increases the expression of BAD ceases.

In certain embodiments, the chemotherapeutic agent is to be administered after the agent that increases the expression of BAD has been administered.

In certain embodiments, the chemotherapeutic agent is to be administered once the level of expression of BAD is increased by at least 5%, or at least 10%, or at least 20%, or at least 30%, or at least 40%, relative to the control. Preferably, the chemotherapeutic agent is to be administered once the level of expression of BAD is increased by at least 10% relative to a control.

In certain embodiments, the agent and chemotherapeutic agent are to be administered simultaneously.

Further according to said first aspect, the chemotherapeutic agent may be selected from the group consisting of PI3-kinase inhibitors, AKT inhibitors, taxanes, antimetabolites, alkylating agents, cell cycle inhibitors, topoisomerase inhibitors and cytotoxic antibodies. The chemotherapeutic agent can be administered in any conventional way, the method of administration being largely dependent on the small molecule signalling inhibitor to be used. Accordingly, administration by inter alia, the parenteral, oral, sublingual, nasal and/or pulmonary routes are envisaged.

Where the chemotherapeutic agent is a PI3-kinase inhibitor, suitable examples include, but are not limited to, wortmannin, LY294002, demethoxyviridin, IC87114, NVP-BEZ235, BAY 80-6946, BKM120, GDC-0941, GDC-9080; including combinations thereof; and pharmaceutically acceptable salts, solvates, hydrates, stereoisomers, clathrates and prodrugs of any of the above.

Where the chemotherapeutic agent is an AKT inhibitor, suitable examples include, but are not limited to, MK-2206, GSK690693, perifosine, PHT-427, AT7867, honokiol, PF-04691502; including combinations thereof; and pharmaceutically acceptable salts, solvates, hydrates, stereoisomers, clathrates and prodrugs of any of the above.

Where the chemotherapeutic agent is a taxane, suitable examples include, but are not limited to, paclitaxel and docetaxel; including combinations thereof; and pharmaceutically acceptable salts, solvates, hydrates, stereoisomers, clathrates and prodrugs of any of the above.

Where the chemotherapeutic agent is an antimetabolite, suitable examples include, but are not limited to, methotrexate, 5-fluorouracil, capecitabin, cytosinarabinoside (Cytarabin), gemcitabine, 6-thioguanin, pentostatin, azathioprin, 6-mercaptopurin, fludarabin and cladribin; including combinations thereof; and pharmaceutically acceptable salts, solvates, hydrates, stereoisomers, clathrates and prodrugs of any of the above. Gemcitabine is an especially preferred antimetabolite. By way of example, gemcitabine may be administered at a dose (per administration) of 800-1200 mg/m$^2$, preferably 900-1100 mg/m$^2$, for example about 1000 mg/m$^2$, or 1000 mg/m$^2$.

Where the chemotherapeutic agent is an alkylating agent, suitable examples include, but are not limited to, mechlorethamine, cyclophosphamide, ifosfamide, trofosfamide, melphalan (L-sarcolysin), chlorambucil, hexamethylmelamine, thiotepa, busulfan, carmustine (BCNU), streptozocin (streptozotocin), dacarbazine (DTIC; dimethyltriazenoimidazol ecarboxamide) temozolomide and oxaliplatin; including combinations thereof; and pharmaceutically acceptable salts, solvates, hydrates, stereoisomers, clathrates and prodrugs of any of the above. Cyclophosphamide and oxaliplatin are especially preferred alkylating agents. By way of example, oxaliplatin may be administered at a dose (per administration) of 65-105 mg/m$^2$, preferably 75-95 mg/m$^2$, for example about 85 mg/m$^2$, or 85 mg/m$^2$. By way of example, cyclophosphamide may be administered at a dose (per administration) of up to 1800 mg/m$^2$, for example 400-1800 mg/m$^2$.

Where the chemotherapeutic agent is a cell cycle inhibitor, suitable examples include, but are not limited to, Epothilone, Vincristine, Vinblastine, UCN-01, 17AAG, XL844, CHI R-124, PF-00477736, CEP-3891, Flavopiridol, berberine, P276-00, terameprocol, isoflavone daidzein, BI2536, BI6727, GSK461364, Cyclapolin, ON-01910, NMS-P937, TAK-960, Ispinesib, Monastrol, AZD4877, LY2523355, ARRY-520, MK-0731, SB743921, GSK923295, Lonafarnib, proTAME, Bortezomib, MLN9708, ONX0912, CEP-18770; including combinations thereof; and pharmaceutically acceptable salts, solvates, hydrates, stereoisomers, clathrates and prodrugs of any of the above; particularly suitable examples of cell cycle inhibitors include, but are not limited to, Hespaeradin, ZM447439, VX-680, MLN-8054, PHA-739358, AT-9283, AZD1152, MLN8237, ENMD2076, SU6668; including combinations thereof; and other inhibitors of Aurora kinases; and pharmaceutically acceptable salts, solvates, hydrates, stereoisomers, clathrates and prodrugs of any of the above.

In certain embodiments, the chemotherapeutic agent is an antimetabolite, preferably gemcitabine.

In certain embodiments, the chemotherapeutic agent is an alkylating agent, preferably oxaliplatin.

The present invention may be used to treat cancers including sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia). In particular aspects, a tumour or cancer includes a lung adenocarcinoma, lung carcinoma, diffuse or interstitial gastric carcinoma, colon adenocarcinoma, prostate adenocarcinoma, esophagus carcinoma, breast carcinoma, pancreas adenocarcinoma, ovarian adenocarcinoma, adenocarcinoma of the adrenal gland, adenocarcinoma of the endometrium or uterine adenocarcinoma.

Tumours and cancers include benign, malignant, metastatic and non-metastatic types, and include any stage (I, II, III, IV or V) or grade (G1, G2, G3, etc.) of tumour, or cancer, or metastasis that is progressing, worsening, stabilized or in remission. Cancers that may be treated according to the invention include but are not limited to: bladder, blood, bone, bone marrow, brain, breast, colon, esophagus, gastrointestines, gum, head, kidney, liver, lung, nasopharynx, neck, ovary, prostate, skin, stomach, testis, tongue, or uterus. Preferably, the cancer is selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour.

In certain embodiments, the cancer to be treated is selected from the list consisting of lung cancer, colon cancer, breast cancer, pancreatic cancer, lymphoma or glioma.

In certain embodiments, the cancer to be treated is preferably breast cancer.

In certain embodiments, the cancer to be treated is lung cancer or colon cancer. Preferably, the cancer to be treated is colon cancer. Preferably, the cancer to be treated is colon cancer.

In a second aspect of the invention, there is provided a method of selecting a subject having a cancer for treatment with an agent that increases the level of expression of BAD, comprising the steps of: (a) obtaining a biological sample from the cancer subject suspected in need thereof: (b) measuring the concentration of BAD within the sample; and (c) comparing the measured concentration of BAD to a reference value, wherein if the subject has an BAD concentration roughly equivalent to or less than the reference value, the subject is selected for administration with an agent that increases the expression of BAD.

The term "roughly" is used herein to provide literal support for the exact value that the term precedes, as well as a value that is near to or approximately the value that the term precedes. In determining whether the value is near to or approximately a specifically recited value, the near or approximating unrecited value may be a value which, in the context in which it is presented, provides the substantial equivalent of the specifically recited value. For example, "roughly" may mean that the value is within 1%, or 2%, or 5% of the reference value.

In certain embodiments of the second aspect, the method can be used to monitor the therapeutic efficacy of an agent that increases the expression of BAD, comprising performing steps (a) to (c) according to the second aspect of the invention after a subject has been administered the agent.

Monitoring the level of expression of BAD after administration of the agent enables a chemotherapeutic agent to be subsequently administered once the subject is sensitized to the chemotherapeutic agent. If the BAD concentration is at least 5%, or at least 10%, or at least 20%, or at least 30%, or at least 40%, preferably at least 10% greater than the reference value after administration of the agent, the subject can be selected for administration with a chemotherapeutic agent. Alternatively, if the BAD concentration is less than 5%, 10%, 20%, 30% or 40% greater than the reference value, the subject can be selected for re-administration of the agent that increases the expression of BAD. Preferably, when the concentration of BAD is less than 10% greater than the reference value after administration of the agent, the subject is to be selected for re-administration of the agent that increases the expression of BAD.

According to the second aspect of the invention, the phrases "reference value" and "control value" are herein used interchangeably. The "reference" value for use in the method can be the level of expression of BAD determined from biological sample obtained from a healthy subject. As used herein, a "healthy subject" refers to a subject who is not suffering from cancer. The reference value may be determined by measuring the level of expression of BAD in the sample obtained from a healthy individual at the time the method of the second aspect of the invention is performed. Alternatively, the reference value may be a pre-determined value from a prior measurement of the level of expression of BAD in an equivalent sample obtained from a healthy individual. When monitoring the therapeutic efficacy of the agent that increases the expression of BAD, the reference value may be that derived from a healthy individual, or the reference value may be the BAD concentration measured in the sample previously obtained from the subject, i.e. the reference value may be the level of expression of BAD in a sample obtained from the subject prior to administration of the agent.

In certain embodiments, the biological sample obtained from the subject for use in the method is blood, plasma, serum, lymph fluid, a tissue, or cells derived from a tissue sample. Preferably, the sample is obtained from a tumour biopsy of the subject. Conventional techniques for obtaining any of the above biological samples from a subject are well known to the person skilled in the art.

In certain embodiments, the level of expression of BAD is determined by performing any method selected from the list consisting of Western blot, mRNA expression analysis, ribosome profiling, flow cytometry, or mass spectrometry. The level of expression of BAD may also be determined using other conventional analytical methods known to the person skilled in the art.

In certain embodiments, the agent that increases the expression of BAD is selected from the group consisting of 6-β-naltrexol, naloxone, methylnaltrexone, or pharmaceutically acceptable salts thereof. Preferably, the agent that increases the expression of BAD is 6-β-naltrexol or a pharmaceutically acceptable salt thereof.

In certain embodiments, the chemotherapeutic agent is selected from group consisting of PI3-kinase inhibitors, AKT inhibitors, taxanes, antimetabolites, alkylating agents, cell cycle inhibitors, topoisomerase inhibitors and cytotoxic antibodies.

In certain embodiments, the cancer subject has a cancer selected from the list consisting of lung cancer, colon cancer, breast cancer, pancreatic cancer, lymphoma or glioma. Preferably, the cancer subject has colon cancer or lung cancer. In certain embodiments, the cancer is colon cancer. In certain embodiments, the cancer is breast cancer.

According to a third aspect of the invention, there is provided a method of screening for an agent that increases the expression of BAD for use according to any embodiment of the first aspect of the invention, comprising the steps of: (a) incubating cells with a test agent; (b) measuring the concentration of BAD after incubation with the test agent; and (c) comparing the increase in the level of expression of BAD between the cells and a control value, wherein if the increase in the level of expression of BAD is at least 5%, or at least 10%, or at least 20%, or at least 30%, or at least 40% relative to a control the agent is identified as an agent for use according to the first aspect of the invention. Preferably, where the agent increases the level of expression of BAD by at least 10% compared to the control, the agent is identified as an agent for use according to any embodiment of the first aspect of the invention.

In order to perform the method of the third aspect of the invention the skilled person could employ any number of standard cell culture techniques routinely used in in vitro drug screening protocols. For example a multi-well in vitro cell culture format could be used, enabling multiple candidate agents to be screened simultaneously at multiple concentrations. Thus, from such a format, the skilled person would be able to determine the most suitable agents by analysing how the expression of BAD increases as a function of agent concentration. In order to determine the level of expression of BAD, any number of known methods in the art, including by not limited to RT-PCR, Western blotting, immunohistochemistry and suitable derivatives of the above, can be performed by the skilled person. The fold change in expression can be determined with reference to a control value derived from a population of cells that have been incubated with either a vehicle agent or no agent at all, where a vehicle agent is a molecule known not to increase the level of expression of BAD. Suitable vehicle agents would be well known to the skilled person, or alternatively a suitable vehicle agent could be an agent that does not increase the expression of BAD as determined from the screening method. Alternatively, the control value may be a predetermined value corresponding to the endogenous level of BAD expression in a population of cells used in the assay.

In an embodiment of the third aspect of the invention, the cells are, or are derived from, an immortalized cell line, preferably of human origin. An "immortalised" cell line refers to a population of cells that due to mutation undergo indefinite proliferation and evade normal cellular senescence. For example the cells may be, or may be derived from, SH-SY5Y, Hep-G2, HEK 293, RAW 264.7, HeLa, MRC-5, A2780, CACO-2, THP 1, A549, PD 30, MCF7, SNL 76/7, C2C12, Jurkat E6.1, U937, L929, 3T3 L1, HL60, PC-12, HT29, OE33, OE19, NIH 3T3, MDA-MB-231, K562, U-87 MG, PD-25, A2780cis, B9, CHO-K1, MDCK, 1321N1, A431, ATDC5, HUVEC, Vero, Fao, J774A.1, MC3T3-E1, J774.2, PNT1A, U-2 OS, HCT 116, MA104, BEAS-2B, NB2-11, BHK 21, NSO, Neuro 2a, T47D, 1301, PNT2, PC-3, TF1, COS-7, MDCK, NCI-322, SK,N.SH, LNCaP.FGC, OE21, PSN1, ISHIKAWA, MFE-280, MG-63, RK 13, EoL-1 cell, VCaP, tsA201, CHO, HT 1080, PANC-1, Saos-2, SK-OV-3, COV434, Hep 3B, A375, AGS, CAKI 2, COLO 205, COR-L23, IMR 32, QT 35, WI 38, HMVII, HT55, or TK6 cells.

According to a fourth aspect of the invention, there is provided a method of treatment of a subject having cancer comprising administration of an anti-cancer agent, characterised in that the subject to be treated has an increase of 10% in the level of expression of BAD in tumour cells, relative to a control.

This aspect of the invention is based on the discovery that tumour cells with an increased level of expression of BAD are more sensitized to the effects of anti-cancer agents. As used herein "sensitized" refers to the increased susceptibility of the cancer cell to cytotoxicity in response to administration of an anti-cancer agent, whereby the increased "sensitivity" is due to an increase in the level of expression of BAD relative to a control. The increase in the level of expression of BAD may be an inherent feature of the tumour cell, or the increase in the level of expression may be induced by administration of an agent that increases the expression of BAD. The increase in the level of expression can be determined with respect to the basal level of expression of BAD in a non-cancerous cell in a subject to be administered the anti-cancer agent In this instance, the basal level of expression in the non-cancerous cell is referred to as the control. Alternatively, the basal level of expression of BAD may be a pre-determined value derived from the level of expression of BAD in a non-cancerous cell in a healthy subject.

In a fourth aspect, there is provided a method of treatment of a subject having cancer comprising administering to the subject an anti-cancer agent, characterised in that the subject to be treated has an increase of 10% in the level of expression of BAD in tumour cells, relative to a control. The level of expression of BAD in the subject may be increased by administering an agent according to the first aspect of the invention.

In a fifth aspect of the invention, there is provided the use of an agent that increases the expression of BAD in the manufacture of a medicament for the treatment of cancer, wherein the medicament is to be administered in conjunction with a chemotherapeutic agent.

In further embodiments of both the fourth and fifth aspects of the invention, said method or said use has the same optional and preferred features as are applicable to the first aspect of the invention.

For use in the invention, there is provided a pharmaceutical composition comprising 6-ß-naltrexol or an analogue thereof or a pharmaceutically acceptable salt of either. The pharmaceutical composition may be provided as an oral solution, a caplet, a capsule, an injectable, an infusible, a suppository, a lozenge or a tablet. In certain embodiments, the pharmaceutical composition is provided in oral dosage forms, particularly as a tablet.

As used herein the term "pharmaceutical composition" means, for example, a mixture containing a specified amount of a therapeutic compound or compounds, e.g. a therapeutically effective amount, in a pharmaceutically acceptable carrier to be administered to a mammal, e.g., a human in order to treat a disease.

As used herein the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term formulation is intended to include the mixture of the active component(s) with encapsulating material as a carrier providing a solid dosage form in which the active compound (with or without other carriers) is surrounded by a carrier which is thus in association with it. Similarly, cachets are included. Tablets, powders, cachets, and capsules can be used as solid dosage forms suitable for oral administration.

The pharmaceutical formulation can be in unit dosage form. In such form, the composition is divided into unit doses containing appropriate quantities of the active component(s). The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

In one embodiment, the 6-ß-naltrexol product to be employed in the present compositions in a solid oral dosage form contains a therapeutically effective amount of 6-ß-naltrexol, which may be, for example, from about 0.01 mg to up to 50 mg, preferably from about 0.01 mg to about 40 mg, most preferably from about 0.01 to about 20 mg of the 6-ß-naltrexol product per tablet; e.g. about 0.01 mg, about 0.05 mg, about 0.1 mg, about 0.3 mg, about 0.5 mg, about 1 mg, about 2 mg, about 3 mg, about 5 mg, about 10 mg, about 20 mg, about 30 mg, about 40 mg or about 50 mg of the 6-ß-naltrexol product per tablet. In certain embodiments, the composition comprises the appropriate amount of dosages of the 6-ß-naltrexol product to account for degradation, if any, of the 6-ß-naltrexol product. In certain embodiments the composition comprises of from 3 mg to 4.5 mg.

The pharmaceutical composition may be provided as a blend of both the 6-ß-naltrexol product and a combination of pharmaceutically acceptable excipients.

As used herein, the term "excipient" refers to a pharmaceutically acceptable ingredient that is commonly used in pharmaceutical technology for the preparation of solid oral dosage formulations. Examples of categories of excipients include, but are not limited to, binders, disintegrants, lubricants, glidants, stabilizers, fillers, and diluents. The amount of each excipient used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2000).

Suitable excipients include magnesium carbonate, magnesium stearate, talc, lactose, lactose monohydrate, sugar, pectin, dextrin, starch, tragacanth, microcrystalline cellulose, methyl cellulose, sodium carboxymethyl cellulose, corn starch, colloidal anhydrous Silica, titanium dioxide, a low-melting wax, cocoa butter, and the like.

In another embodiment, the pharmaceutical composition comprises at least one excipient.

The invention is further illustrated by the following non-limiting examples.

EXAMPLES

Example 1

Determination of the Level of Expression of BAD after Administration of 6-β-Naltrexol In order to determine the effect of 6-β-naltrexol or naltrexone on the level of expression of BAD, pAKT, p21, cyclin B1 and CDK1 HCT116 colon cancer cells were seeded onto 6-well plates at a density of $2\times10^5$ cell/well, and allowed to adhere overnight. Cells were then cultured in the presence of naltrexone or 6-β-naltrexol at concentrations of 10 nM or 10 μM for a further 48 h. Cells were then harvested and processed for measurements of BAD, or pAKT, p21, cyclin B1 and CDK1 using standard immunoblotting techniques.

The results show that 10 μM 6-β-naltrexol increases the level of expression of BAD in HCT116 cells by more than 10%, whereas both concentrations of naltrexone and 10 nM 6-β-naltrexol have a negligible effect on the level of expression of BAD.

Example 2

Increasing the Level of BAD Expression Boosts the Efficacy of Anti-Cancer Agents The impact of combining 6-β-naltrexol with other chemotherapy agents was tested by culturing cells according to a treatment schedule that involved two phases of treatment. The first phase involved priming with 10 nM 6-β-naltrexol or 10 μM 6-β-naltrexol for 48 h, before treatment with another drug for a further 48 h. A549 and HCT116 cells were seeded into 6-well plates at a density of $2\times10^5$ cells/well and left to adhere overnight. Media was removed after 48 h, and cells were rinsed gently with drug-free medium. Fresh culture medium that contained gemcitabine (GEM) or oxaliplatin (OXP) was then added to the cells. The concentrations of the chemotherapy agents used were approximately ¼ IC50, as established previously [Liu W M, Fowler D W, Smith P, Dalgleish A G. Pre-treatment with chemotherapy can enhance the antigenicity and immunogenicity of tumours by promoting adaptive immune responses. Br J Cancer. 2010 Jan. 5; 102(1):115-23. doi: 10.1038/sj.bjc.6605465.]. Cells were then left for a further 48 h before assessment of cell number of viability by cell counting using trypan blue dye as a way of discriminating live and dead cells. Cytostasis was indicated by a reduction in cell number and no associated reduction in cell viability.

Figure 2A:
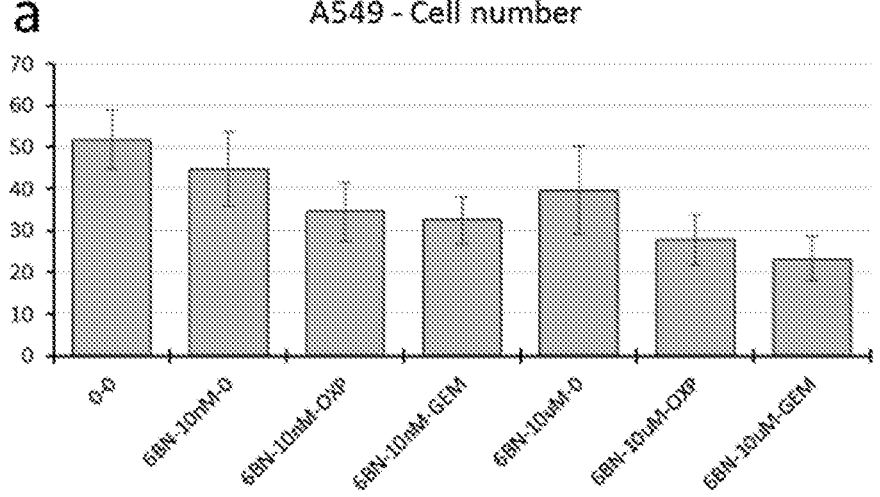
FIG. 2 shows the (a and b) cyostasis and (c and d) cytotoxicity in (a and c) A549 cells and (b and d) HCT116 cells upon co-administration of 10 nM or 10 μM 6-β-naltrexol in combination with GEM or OXP. A control sample of cells were administered where no 6-β-naltrexol was used.
Figure 2A:
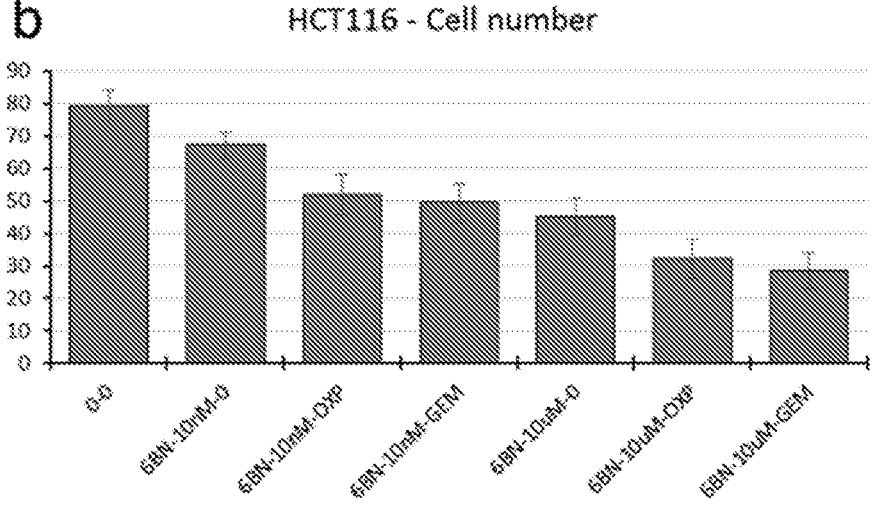
Figure 2B:
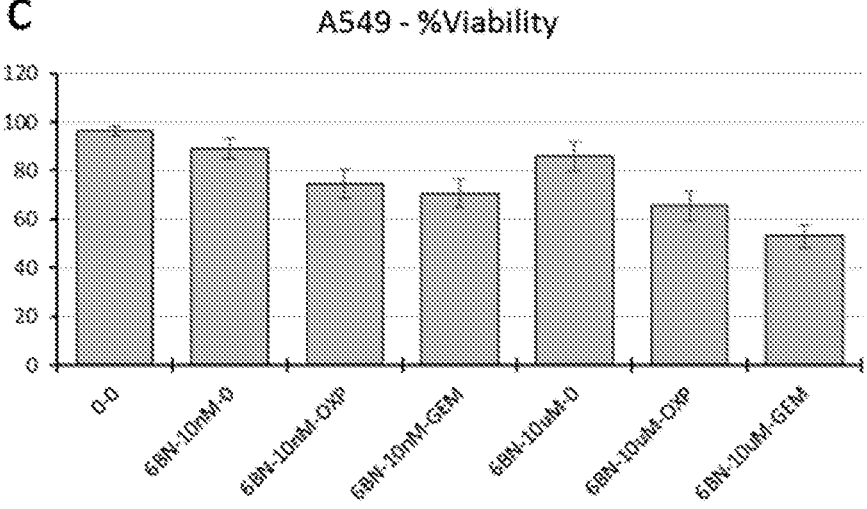
Figure 2B:
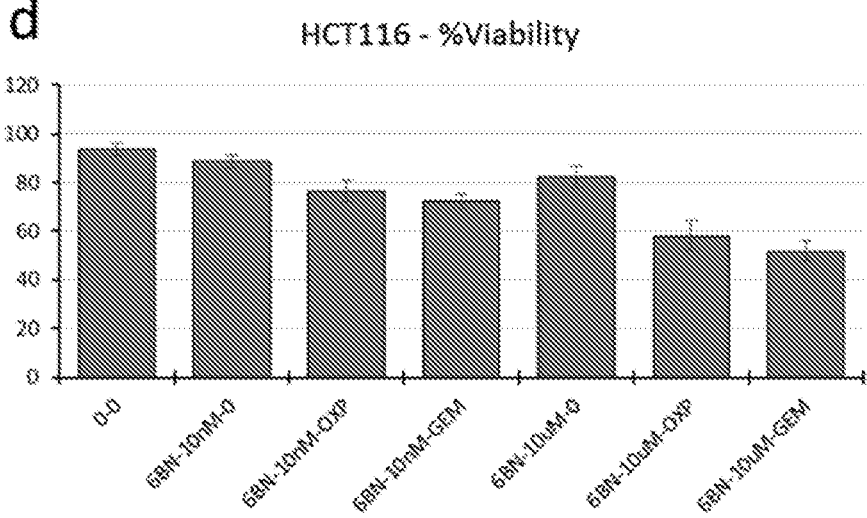

The experiments show that when 6-β-naltrexol is added in an amount effective to raise the level of expression of BAD by at least 10%, the cytotoxic effect of both chemotherapeutic agents is increased. This effect is observed in the absence of any independent increase in cytotoxicity caused by the administration of a 6-β-naltrexol alone (FIG. 2c and d, 10 nM 6BN-0, or 10 μM 6BN-0). Furthermore, the enhanced cytotoxic effect is greater when the level of expression of BAD is more greatly increased (i.e. by administering a greater dose of 6-β-naltrexol.

Thus, the experiments show that an agent that increases the expression of BAD is capable of enhancing the therapeutic efficacy of particular anti-cancer agents.

Example 3

Determination of Effect of 6BN on Cancer Cell Line

Figure 3:
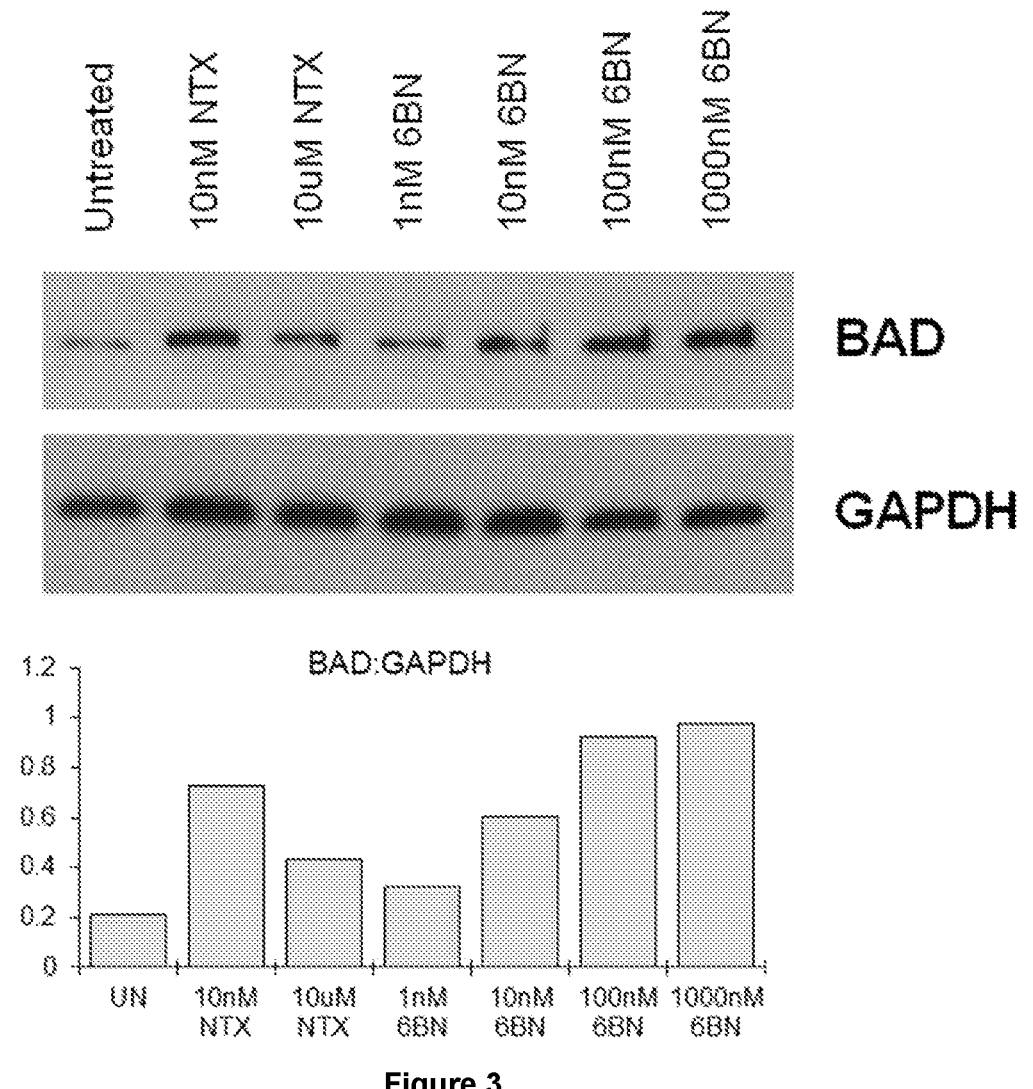
FIG. 3 shows the dose-dependent increase in the level expression of BAD in breast cancer cells in response to different concentrations of 6-β-naltrexol.
Figure 4:
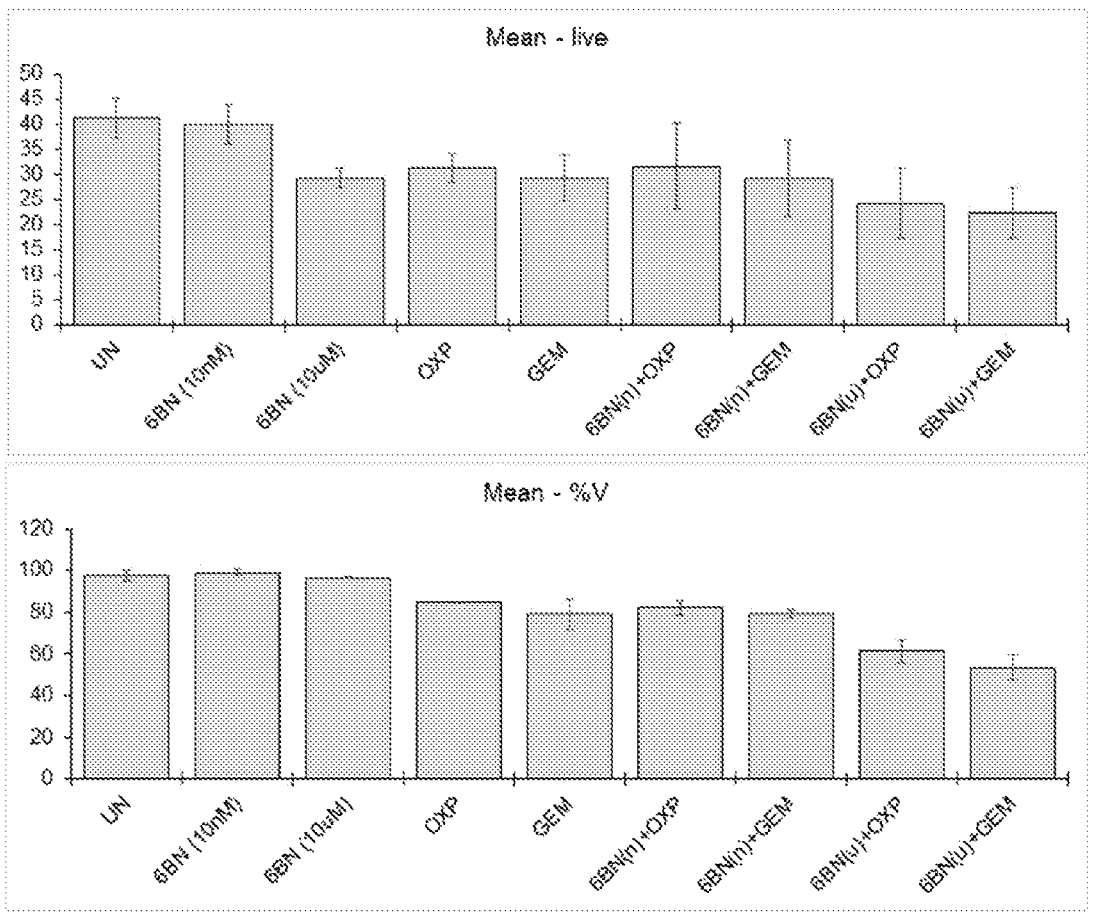
FIG. 4 shows the cytostasis (a) and cytotoxicity (b) in a breast cancer cell line upon administration of 10 nM (6BN (n)) or 10 μM 6-β-naltrexol (6BN(u)) either alone or in combination with gemcitabine (GEM) or oxaliplatin (OXP). Results from controls of cells being administered no agent (UN) or GEM or OXP alone are also shown.

Similar experiments to those performed in A549 and HCT116 cells were completed in the breast cancer cell line MCF-7 to assess the effects of 6BN of protein expression by western blotting, and results indicated 6BN induced a dose dependent increase in the expression of the pro-apoptotic protein BAD (FIG. 3). The effect of combining 6BN with the chemotherapeutic agents gemcitabine or oxaliplatin was tested by culturing MCF-7 cells with 6BN (10 nM or 10 uM) concomitantly with gemcitabine (0.5 uM) or oxaliplatin (0.5 uM). Cell number and viability was then assessed after 48 h using trypan blue dye exclusion as a means to discriminate live/dead cells. Results indicated that the combination of 10 uM 6BN with any chemotherapy caused the greatest effect on cell viability (FIG. 4).

The invention claimed is:

1. A packaged preparation comprising:
(a) a pharmaceutical composition in a solid dosage form comprising from 0.01 mg to up to 40 mg per tablet of an agent that increases the expression of BAD (Bcl2-associated agonist cell death), wherein the agent is 6-β-naltrexol, or pharmaceutically acceptable salts thereof, and
(b) a chemotherapeutic agent, wherein the chemotherapeutic agent is selected from the group consisting of a class of antimetabolite chemotherapeutic agents and a class of alkylating chemotherapeutic agents
in the treatment of cancer, wherein the cancer is selected from the group consisting of colon cancer, breast cancer and lung cancer.

2. The packaged preparation according to claim 1, wherein the agent is to be administered in an amount effective to increase the expression of BAD, by at least 5%, or at least 10%, or at least 20%, or at least 30%, or at least 40%, relative to a control.

3. The packaged preparation according to claim 1 or 2, wherein the 6-β-naltrexol is to be administered in an amount effective to increase the blood plasma concentration of 6-β-naltrexol to from 0.34 ng/ml to 3,400 ng/ml, or greater.

4. The packaged preparation according to claim 3, wherein the 6-β-naltrexol is to be administered in an amount effective to increase the blood plasma concentration of 6-β-naltrexol to from 34 ng/ml to 3,400 ng/ml, or greater.

5. The packaged preparation according to claim 4, wherein the 6-μ-naltrexol is to be administered in an amount effective to increase the blood plasma concentration of 6-β-naltrexol to from 340 ng/ml to 3,400 ng/ml.

6. The packaged preparation according to claim 1, wherein the pharmaceutical composition is for separate, sequential or simultaneous administration with the chemotherapeutic agent.

7. The packaged preparation according to claim 6, wherein the pharmaceutical composition and chemotherapeutic agent are to be administered sequentially or separately.

8. The packaged preparation pharmaceutical according to claim 6 or 7, wherein the chemotherapeutic agent is to be administered after the pharmaceutical composition comprising the agent that increases the expression of BAD has been administered.

9. The packaged preparation according to claim 6, wherein the chemotherapeutic agent is to be administered once the level of expression of BAD is increased by at least 5% relative to a control.

10. The packaged preparation according to claim 6, wherein the pharmaceutical composition comprising the agent and the chemotherapeutic agent are administered simultaneously.

11. The packaged preparation according to claim 6, wherein the chemotherapeutic agent is selected from the group consisting of PI3-kinase inhibitors, AKT inhibitors, taxanes, antimetabolites, alkylating agents, cell cycle inhibitors, topoisomerase inhibitors and cytotoxic antibodies.

12. The packaged preparation according to claim 11, wherein the chemotherapeutic agent is an antimetabolite.

13. The packaged preparation according to claim 11, wherein the chemotherapeutic agent is an alkylating agent.

14. The packaged preparation according to claim 1, wherein the cancer is lung cancer or colon cancer.

15. The packaged preparation according to claim 1, wherein the cancer is breast cancer.

16. The packaged preparation of claim 1, wherein the pharmaceutical composition comprises from 0.01 mg to up to 30 mg per tablet of 6-β-naltrexol.

17. The packaged preparation of claim 1, wherein the pharmaceutical composition comprises from 0.01 mg to up to 20 mg per tablet of 6-β-naltrexol.

18. The packaged preparation of claim 1, wherein the pharmaceutical composition comprises from 0.01 mg to up to 10 mg per tablet of 6-β-naltrexol.

* * * * *